US006623982B1

(12) United States Patent
Liberti et al.

(10) Patent No.: US 6,623,982 B1
(45) Date of Patent: Sep. 23, 2003

(54) INCREASED SEPARATION EFFICIENCY VIA CONTROLLED AGGREGATION OF MAGNETIC NANOPARTICLES

(75) Inventors: Paul A. Liberti, Huntingdon Valley, PA (US); Galla Candra Rao, Princeton, NJ (US); Leon W. M. M. Terstappen, Huntingdon Valley, PA (US)

(73) Assignee: Immunivest Corporation, Wilmington, DE (US)

( * ) Notice: Subject to any disclaimer, the term of this patent is extended or adjusted under 35 U.S.C. 154(b) by 0 days.

(21) Appl. No.: 09/351,515

(22) Filed: Jul. 12, 1999

(51) Int. Cl.$^7$ ............................................. G01N 33/553
(52) U.S. Cl. ...................... 436/526; 436/518; 436/537; 436/538; 436/18; 436/164; 436/166; 436/177; 436/805; 436/824; 435/7.1; 435/967; 435/7.92; 435/7.93; 435/7.94; 435/7.95
(58) Field of Search ................................. 436/518, 526, 436/537, 538, 18, 164, 166, 177, 805, 824; 435/7.1, 967, 7.92–7.95

(56) References Cited

U.S. PATENT DOCUMENTS

| 4,253,844 A | * | 3/1981 | Limet et al. .................. 23/230 |
| 4,812,401 A | | 3/1989 | Tarnowski et al. |
| 4,868,130 A | | 9/1989 | Hargreaves |
| 5,186,827 A | * | 2/1993 | Liberti et al. ............... 210/222 |
| 5,200,084 A | * | 4/1993 | Liberti et al. ............... 210/695 |
| 5,405,743 A | | 4/1995 | Tarnowski et al. |
| 5,439,586 A | | 8/1995 | Richards et al. |
| 5,466,574 A | * | 11/1995 | Liberti et al. .................. 435/5 |
| 5,622,831 A | * | 4/1997 | Liberti et al. ............... 435/7.21 |
| 5,635,356 A | | 6/1997 | Packard et al. |
| 5,665,582 A | | 9/1997 | Kausch et al. |
| 5,698,271 A | | 12/1997 | Liberti et al. |
| 5,779,892 A | * | 7/1998 | Miltenyi et al. ............. 210/222 |
| 5,876,593 A | * | 3/1999 | Liberti et al. ................ 210/95 |
| 6,004,743 A | | 12/1999 | Kenyon et al. |
| 6,013,188 A | * | 1/2000 | Terstappen et al. ......... 210/695 |
| 6,117,985 A | | 9/2000 | Thomas et al. |
| 6,121,055 A | | 9/2000 | Hargreaves |
| 6,146,838 A | * | 11/2000 | Williams et al. ............. 435/7.2 |
| 6,150,181 A | * | 11/2000 | Halbreich et al. .......... 436/526 |
| 6,207,380 B1 | | 3/2001 | Billing-Medel et al. |

FOREIGN PATENT DOCUMENTS

GB          2 152 664 A        8/1985

* cited by examiner

Primary Examiner—Christopher L. Chin
Assistant Examiner—Pensee T. Do
(74) Attorney, Agent, or Firm—Dann, Dorfman, Herrell and Skillman

(57) ABSTRACT

Compositions and methods are disclosed which enhance the microscopic observation and analysis of biological entities such as cells, bacteria and viruses by eliminating interfering magnetic clusters created by naturally occurring aggregators of colloidal magnetic particles. Additionally means for significantly enhancing the magnetic isolation of low antigen density target cells from biological samples are disclosed.

33 Claims, 1 Drawing Sheet

INCREASED SEPARATION EFFICIENCY VIA CONTROLLED AGGREGATION OF MAGNETIC NANOPARTICLES

FIELD OF THE INVENTION

This invention relates to the fields of bioaffinity separations and diagnostic testing of biological samples. More specifically, the invention provides compositions and methods which, may be used in magnetic separation assays and enrichment procedures for controlling endogenous magnetic particle aggregation factors which, if uncontrolled, would obscure visualization of isolated entities. Also provided are methods for constructing and synthesizing reversible aggregation factors and the resulting compositions which simultaneously enhance recovery of rare biological substances while facilitating observation of substances so isolated.

BACKGROUND OF THE INVENTION

Several publications are referenced in this application by numerals in parentheses in order to more fully describe the state of the art to which this invention pertains. The disclosure of each of these publications is incorporated by reference herein.

Many laboratory and clinical procedures employ bio-specific affinity reactions. Such reactions are commonly utilized in diagnostic testing of biological samples, or for the separation of a wide range of target substances, especially biological entities such as cell, viruses, proteins, nucleic acids and the like. Various methods are available for analyzing or separating the above-mentioned target substances based upon complex formation between the substance of interest and another substance to which the target substance specifically binds. Separation of complexes from unbound material may be accomplished gravitationally, e.g. by settling, or, alternatively, by centrifugation of finely divided particles or beads coupled to the target substance. If desired, such particles or beads may be made magnetic to facilitate the bound/free separation step. Magnetic particles are well known in the art, as is their use in immune and other bio-specific affinity reactions. See, for example, U.S. Pat. No. 4,554,088 and *Immunoassays for Clinical Chemistry*, pp. 147–162, Hunter et al. eds., Churchill Livingston, Edinborough (1983). Generally, any material which facilitates magnetic or gravitational separation may be employed for this purpose. However, in the past 20 years the superiority of magnetics for performing such separations has led to its use in many applications.

Magnetic particles generally fall into two broad categories. The first category includes particles that are permanently magnetizable, or ferromagnetic. The second category comprises particles that demonstrate bulk magnetic behavior only when subjected to a magnetic field. The latter are referred to as magnetically responsive particles. Materials displaying magnetically responsive behavior are sometimes described as superparamagnetic. However, materials exhibiting bulk ferromagnetic properties, e.g., magnetic iron oxide, may be characterized as superparamagnetic only when provided in crystals of about 30 nm or less in diameter. Larger crystals of ferromagnetic materials, by contrast, retain permanent magnet characteristics after exposure to a magnetic field and tend to aggregate thereafter due to strong particle-particle interactions. Magnetic particles can be classified as large (1.5 to about 50 microns), small (0.7–1.5 microns), and colloidal or nanoparticles (<200 nm). The latter are also called ferrofluids or ferrofluid-like and have many of the properties of classical ferrofluids. Liberti et al pp 777–790, E. Pelizzetti (ed) "Fine Particles Science and Technology" Kluwer Acad. Publishers, Netherlands, 1996.

Small magnetic particles are quite useful in analyses involving bio-specific affinity reactions, as they are conveniently coated with biofunctional polymers (e.g., proteins), provide very high surface areas and give reasonable reaction kinetics. Magnetic particles ranging from 0.7–1.5 microns have been described in the patent literature, including, by way of example, U.S. Pat. Nos. 3,970,518; 4,018,886; 4,230,685; 4,267,234; 4,452,773; 4,554,088; and 4,659,678. Certain of these particles are disclosed to be useful solid supports for immunologic reagents.

In addition to the small magnetic particles mentioned above, there are a class of large magnetic particles ranging in size from approximately 1.5–50 microns, which also have superparamagnetic behavior. Typical of such materials are those invented by Ugelstad (U.S. Pat. No. 4,654,267) and manufactured by Dynal, (Oslo, Norway). The Ugelstad process involves the synthesis of polymer particles which are caused to swell and magnetite crystals are embedded in the swelled particles. Other materials in the same size range are prepared by synthesizing the particle in the presence of dispersed magnetite crystals. This results in the trapping of magnetite crystals in a polymer matrix, thus making the resultant materials magnetic. In both cases, the resultant particles have superparamagnetic behavior, which is manifested by the ability to disperse readily upon removal of the magnetic field. Unlike magnetic colloids or nanoparticles, these materials, as well as small magnetic particles, are readily separated with simple laboratory magnetics because of the mass of magnetic material per particle. Thus, separations are effected in gradients from as low as a few hundred gauss/cm on up to about 1.5 kilogauss/cm. Colloidal magnetic particles, (below approximately 200 nm),on the other hand, require substantially higher magnetic gradients because of their diffusion energy, small magnetic mass per particle and Stokes drag. U.S. Pat. No. 4,795,698 to Owen et al. relates to polymer-coated, colloidal, superparamagnetic particles. Such particles are manufactured by precipitation of a magnetic species in the presence of a biofunctional polymer. The structure of the resulting particles, referred to herein as single-shot particles, has been found to be a micro-agglomerate in which one or more ferromagnetic crystallites having a diameter of 5–10 nm are embedded within a polymer body having a diameter on the order of 50 nm. The resulting particles exhibit an appreciable tendency to remain in aqueous suspension for observation periods as long as several months. U.S. Pat. No. 4,452,773 to Molday describes a material similar in properties to those described in Owen et al., which is produced by forming magnetite and other iron oxides from $Fe^{+2}/Fe^{+3}$ via base addition in the presence of very high concentrations of dextran. Materials so produced have colloidal properties and have proved to be very useful in cell separation. This technology has been commercialized by Miltenyi Biotec, Bergisch Gladbach, Germany.

Another method for producing superparamagnetic colloidal particles is described in U.S. Pat. No. 5,597,531. In contrast to the particles described in the Owen et al. patent, these latter particles are produced by directly coating a biofunctional polymer onto pre-formed superparamagnetic crystals which have been dispersed, e.g., by sonic energy into quasi-stable crystalline clusters ranging in size from about 25–120 nm. The resulting particles, referred to herein as direct coated (DC) particles, exhibit a significantly larger magnetic moment than Owen et al. or Molday nanoparticles of the same overall size and can be separated effectively in magnetic gradients greater than about 6 kGauss/cm.

Magnetic separation techniques are known wherein a magnetic field is applied to a fluid medium in order to separate ferromagnetic bodies from the fluid medium. In contrast, the tendency of colloidal superparamagnetic particles to remain in suspension, in conjunction with their relatively weak magnetic responsiveness, requires the use of high-gradient magnetic separation (HGMS) techniques in order to separate such particles from a fluid medium in which they are suspended. In HGMS systems, the gradient of the magnetic field, i.e., the spatial derivative, exerts a greater influence upon the behavior of the suspended particles than is exerted by the strength of the field at a given point. High gradient magnetic separation is useful for separating a wide variety of magnetically labeled biological materials, including eukaryotic and prokaryotic cells, viruses, nucleic acids, proteins, and carbohydrates. In methods known heretofore, biological material has been separable by HGMS, provided at least one characteristic determinant is present on the material, which is capable of being specifically recognized and bound to a receptor, such as an antibody, antibody fragment, specific binding protein (e.g., protein A, streptavidin), lectin, and the like. HGMS systems can be divided into two broad categories. One such category includes magnetic separation systems which employ a magnetic circuit that is entirely situated externally to a separation chamber or vessel. Examples of such external separators (or open field gradient separators) are described in U.S. Pat. No. 5,186,827. In several of the embodiments described in the '827 patent, the requisite magnetic field gradient is produced by positioning permanent magnets around the periphery of a non-magnetic container such that the like poles of the magnets are in a field-opposing configuration. The extent of the magnetic field gradient within the test medium obtainable in such a system is limited by the strength of the magnets and the separation distance between the magnets. Hence, there exists a finite limit to gradients that can be obtained with external gradient systems. In a co-pending application Ser. No. 60/098,021, means for maximizing radial gradients and methods for maximizing separation efficiency via novel vessel designs are disclosed.

Another type of HGMS separator utilizes a ferromagnetic collection structure that is disposed within the test medium in order to: (1) intensify an applied magnetic field; and (2) produce a magnetic field gradient within the test medium. Previously disclosed internal HGMS systems comprise fine steel wool or gauze packed within a column that is situated adjacent to a magnet. The applied magnetic field is concentrated in the vicinity of the steel wires so that suspended magnetic particles will be attracted toward, and adhere to, the surfaces of the wires. The gradient produced on such wires is inversely proportional to the wire diameter whereas the magnetic "reach" decreases with diameter. Hence, very high gradients can be generated.

One major drawback of internal gradient systems is that the use of steel wool, gauze material, steel microbeads or the like, may entrap non-magnetic components of the test medium by capillary action in the vicinity of intersecting wires or within interstices between intersecting wires. Various coating procedures have been applied to such internal gradient columns (U.S. Pat. Nos. 5,693,539; 4,375,407), however, the large surface area in such systems still creates recovery problems due to absorption. Hence, internal gradient systems are not desirable, particularly when recovery of very low frequency captured entities is the goal of the separation. Further, these systems make automation difficult and costly.

On the other hand, HGMS approaches using external gradients for cell separation provide a number of conveniences. Firstly, simple laboratory tubes such as test tubes, centrifuge tubes or even vacutainers (used for blood collection) can be employed. When external gradients are of the kind in which separated cells are effectively monolayered, as is the case with quadrupole/hexapole devices (U.S. Pat. No. 5,186,827) or the opposing dipole arrangement described in U.S. Pat. No. 5,466,574, washing of cells or subsequent manipulations are facilitated. Further, recoveries of cells from tubes or similar containers is a simple and efficient process. This is particularly the case when compared to recoveries from high gradient columns. Such separation vessels also provide another important feature which is the ability to reduce volume of the original sample. For example, if a particular human blood cell subset, (e.g. magnetically labeled CD 34+ cells), is isolated from blood diluted 20% with buffer to reduce viscosity, a 15 ml conical test tube may be employed as the separation vessel in an appropriate quadrupole magnetic device. After appropriate washes and/or separations and resuspensions to remove non-bound cells, CD34+ cells can very effectively be resuspended in a volume of 200 $\mu$l. This can be accomplished, for example, by starting with 12 ml of solution (blood, ferrofluid and dilution buffer) in a 15 ml conical test tube, performing a separation, discarding the "supernatant" and subsequent wash "supernatants" and resuspending the recovered cells in 3 ml of appropriate cell buffer. A second separation is then performed which may include additional separation/wash steps (as might be necessary for doing labeling/staining reactions) and finally the isolated cells are easily resuspended in a final volume of 200 $\mu$l. By reducing volume in this sequential fashion, and employing a vortex mixer for resuspension, cells adhered to the tube above the resuspension volume are recovered into the reduced volume. When done carefully and rapidly in appropriately treated vessels, cell recovery is quite efficient, ranging between 70–90%.

The efficiency with which magnetic separations can done and the recovery and purity of magnetically labeled cells will depend on many factors. These include such considerations as the number of cells being separated, the receptor density of such cells, the magnetic load per cell, the non-specific binding (NSB) of the magnetic material, the technique employed, the nature of the vessel, the nature of the vessel surface, the viscosity of the medium and the magnetic separation device employed. If the level of non-specific binding of a system is substantially constant, as is usually the case, then as the target population decreases so does the purity. As an example, a system with 0.2% NSB that recovers 80% of a population which is at 0.25% in the original mixture will have a purity of 50%. Whereas if the initial population were at 1.0%, the purity would be 80%. Not as obvious is the fact that the smaller the population of a targeted cell, the more difficult it will be to magnetically label and to recover. Furthermore, labeling and recovery will markedly depend on the nature of magnetic particle employed. For example, when cells are incubated with large magnetic particles, such as Dynal beads, the cells are labeled through collisions created by mixing of the system as the beads tend to be too large to diffuse. Thus, if a cell were present in a population at a frequency of 1 cell/ml of blood or even less, as could be the case for tumor cells in very early cancers, then the probability of labeling target cells will be related to the numbers of magnetic particles added to the system and the length of time of mixing. Since mixing of cells with such particles for substantial periods of time will be deleterious, it becomes necessary to increase particle concentration as much a possible. There is, however, a limit to the quantity of magnetic particle that can be added to the system, in that one can substitute a system comprising a rare cell mixed in with other blood cells with one comprising a rare cell mixed in with large quantities of magnetic particles upon separation, in which case the ability to enumerate the cells of interest or to examine them is not markedly improved.

There is another drawback to the use of large particles to isolate cells having rare frequencies (1–50 cells/ml of blood). Despite the fact that large magnetic particles allow the use of external gradients of very simple design and relatively low magnetic gradient, large particles tend to cluster around cells in a cage-like fashion making them difficult to "see" or to analyze. Hence, the particles must be released before analysis, and releasing the particles often introduces other complications.

In theory, colloidal magnetic particles, used in conjunction with high gradient magnetic separation, should be the method of choice for separating a cell subset of interest from a mixed population of eukaryotic cells, particularly if the subset of interest comprises only a small fraction of the entire population. With appropriate magnetic loading, sufficient force is exerted on a cell, facilitating its isolation even in a media as viscous as moderately diluted whole blood. As noted, colloidal magnetic materials below about 200 nanometers will exhibit Brownian motion which markedly enhances their ability to collide with and magnetically label rare cells. This is demonstrated in U.S. Pat. No. 5,541,072, where results of very efficient tumor cell purging experiments are described employing 100 nm colloidal magnetic particles (ferrofluids). Just as importantly, colloidal materials at or below the size range noted do not generally interfere with viewing of cells. Cells so retrieved can be examined by flow cytometry with minimal forward scattering effects or by microscopy employing visible or fluorescent techniques. Because of their diffusive properties, such materials, in contrast to large magnetic particles, readily "find" and magnetically label rare biological entities such as tumor cells in blood.

There is, however, a significant problem which arises in the use of ferrofluid-like materials for cell separation in external field gradient systems which, for reasons given above, is the device design of choice. Direct monoclonal antibody conjugates of Owen et al. materials or Molday nanoparticles, such as those produced by Miltenyi Biotec, do not have sufficient magnetic moment for use in cell selection employing the best available external magnetic gradient devices, such as the quadrupole or hexapole magnetic devices described in U.S. Pat. No. 5,186,827. When used for separations in moderately diluted whole blood, they are even less effective. Using similar materials, which are substantially more magnetic, as described in U.S. Pat. No. 5,698,271, more promising results have been obtained. In model spiking experiments, it has been found that SKBR3 cells (breast tumor line), which have a high EpCAM (epithelial cell-adhesion molecule) determinant density, are efficiently separated from whole blood with direct conjugates of anti EpCAM MAb ferrofluids even at very low spiking densities (1–5 cells/ml blood). On the other hand, PC3 cells (a prostate tumor line) which have low antigen density are separated at significantly lower efficiency. Most likely this is a consequence of inadequate magnetic loading onto these low density receptor cells.

From the foregoing discussion, it would be advantageous to provide a magnetic separation system which combines the beneficial properties of both colloidal magnetic materials and large magnetic particles (e.g., diffusion based labeling and large magnetic moment, respectively) for separations involving rare events or for cells with very low density receptors. One could envision starting a separation process with a magnetic colloidal or nanoparticle which, due to their Brownian motion, would rapidly find and label cells in rare numbers or cells with very low density receptors. Once that labeling is achieved, it would be desirable to convert the magnetic moment of the nanoparticle to a value similar to that of a large magnetic particle. In that way, magnetically labeled entities could be separated in the kinds of gradient fields used for larger particles, e.g., a simple external field gradient separator. In the case of very low density receptor cells, which are recovered inefficiently even in high gradient external field separators, use of such a principle would clearly increase the efficiency of separation. In applications where cells are to be analyzed or used for some biological purpose following separation, it would also be very desirable to be able to convert the magnetic moment of the labeled entity back to that of its original colloidal magnetic labeling density. This approach would permit separation from excessive magnetic material, which would facilitate subsequent analysis or use.

U.S. Pat. No. 5,466,574 to Liberti et al., describes a system which has some of the foregoing features regarding "loading on" of magnetic materials onto cells. It was discovered that when cells were first labeled with specific monoclonal antibodies (with or without biotinylation) followed by magnetic labeling with goat anti-mouse ferrofluid or with streptavidin-ferrofluid (respectively), separation was enhanced in the presence of excess monoclonal antibody. The unique ability of ferrofluids to create this "no wash" enhancing procedure is due to immunochemical crosslinking of free ferrofluid in solution to ferrofluid-bound target cells. Ferrofluid bound to monoclonal antibody on cells, in turn, binds to free ferrofluid in solution via free monoclonal antibody. This results in immunochemical clusters of monoclonal antibody/ferrofluid "growing" off of monoclonal antibody labeled cell determinants (referred to as chaining). Thus, magnetic colloid is "artificially" loaded onto cells making them more magnetic and easier to separate. The phenomenon was found to obey immunochemical rules, in that a high excess of monoclonal antibody resulted in a decrease in chaining (monoclonal excess zone) and a loss of separation efficiency. Similarly high levels of ferrofluid also reduced chaining (ferrofluid excess zone). Chaining has been found to be useful for purging unwanted cells, e.g. tumor cells, in bone marrow or peripheral blood "grafts." By this method, very high levels of magnetic material (visible brown rims around cells, as observed via microscopy) can be loaded onto target cells giving rise to very efficient separation in high gradient fields of only 8–12 kGauss/cm gradients. On the other hand, cells labeled with "monomeric" ferrofluid were found to separate less efficiently in the same gradient.

In attempts to use chaining for isolating rare cells from whole blood, several problems have been encountered. First, although spiked cells are, indeed, efficiently recovered, they are so densely covered with ferrofluid (chaining) that the ability to analyze them is markedly reduced. Hence this approach is not ideal for applications wherein the positively selected cells are to be observed via microscopy or flow cytometry. Additionally, chaining seems to promote non-specific binding. In summary, designing a chaining-based assay where the level of chaining simultaneously gives rise to separation enhancement, non-obstructed viewing of the isolated cells and acceptable levels of non-specific binding is extraordinarily difficult. The chaining reaction is difficult to control because it requires immunochemical stoichiometry. For example, most (>99%) of the added monoclonal antibody (or tagging ligand) will always be free in solution regardless of the affinity of the antibodies. Hence, the amount of ferrofluid required to achieve immunochemical equivalence (where the best separations take place via chaining) generally leads to more chaining than is desired, particularly in the case where the selected cell is to be viewed and/or further studied. Chaining can be lessened by concurrent decreases in labeling monoclonal antibody and added ferrofluid, however this results in a sacrifice of separation efficiency. Another drawback to the use of chaining to enhance separation is the inability to, in some practical manner, reverse chaining. If chaining could be reversed and the concomitant increase in non-specific binding decreased, the phenomenon would provide a viable approach to enabling the desired "loading on" of magnetic material. Another disadvantage of this method is that a two step reaction is required, i.e., reaction of targets with primary monoclonal antibody in a first step followed by repetition with ferrofluid specific for primary monoclonal antibody in the second step. This approach cannot be used in assays where primary antibody is directly conjugated to ferrofluid.

U.S. Pat. No. 5,108,933 to Liberti et al. discloses the use of weakly magnetic colloidal materials such as those described by Owen et al. or Molday in immunoassays employing external field magnetic separators. Such materials are described therein as agglomerable and resuspendable colloidal magnetic materials which remain substantially undisturbed in an external magnetic field system, for example, those commercially available at that time (Ciba Corning, Wampole, Mass.; Serono Diagnostics, Norwell, Mass.). By contrast, materials made by the process disclosed in the '531 patent being substantially more magnetic, as noted above, will separate in those separators. In the '933 patent means for converting the colloid to an agglomerate are disclosed so as to make them separable in those separators. Thus, such materials could be used for performing the bound/free separation step of immunoassays. There is no mention in '933 for the need of, or methods for reversing agglomeration reactions.

In light of the foregoing and recent discoveries of naturally occurring ferrofluid aggregation factors, the present inventors have recognized the need for compositions and methods for controlling aggregation of ferrofluid by endogenous factors during the isolation and immunochemical characterization of rare target bioentities. Such compositions and methods may be used to advantage to facilitate analysis and observation of bioentities so isolated. Further, this invention also permits the use of substantially less magnetic reagent as well as the opportunity to use lower magnetic gradients. In the case of a fixed gradient, the invention provides for the capture or isolation of entities which might have otherwise had insufficient magnetic labeling to be captured.

SUMMARY OF THE INVENTION

In accordance with the present invention, methods, compositions and kits are provided for controlling the aggregation of ferromagnetic nanoparticles by endogenous aggregation factors. Ferrofluid aggregation often presents problems during subsequent viewing of the isolated targets. The methods of the invention facilitate visualization of the isolated bioentities by allowing the investigator to control the level of aggregation. In one embodiment of the invention, a method is provided for inhibiting the aggregation of magnetic nanoparticles on the surface of isolated target entities. The method comprises obtaining a biological specimen suspected of containing a target bioentity. Next, immunomagnetic suspensions are prepared by mixing the specimen with colloidal, magnetic particles coupled to a biospecific ligand having affinity for at least one characteristic determinant of the target bioentity. The immunomagnetic suspension is thereafter subjected to a magnetic field to obtain target bioentity enriched fractions. Optionally, the fractions are then examined to determine the characteristics of the target bioentity so isolated. Inhibition of ferrofluid aggregation facilitates subsequent analysis of cells as aggregates of ferrofluid on the cell surface are eliminated. The absence of such aggregates is important for several types of analyses including, for example, flow cytometry and immunofluorescence microscopy.

The reagents provided herein efficiently inhibit or remove endogenous aggregation factors. The factor removal or inhibition step may be performed before or simultaneously with the addition of ferrofluid to the biological specimen for separation and enrichment.

To further characterize target bioentities isolated using the methods of the invention, the method optionally includes the steps of adding to the target bioentity enriched fraction at least one biospecific reagent which recognizes and effectively labels at least one additional characteristic determinant on said target bioentity. The labeled target bioentities are then separated in a magnetic field to remove unbound biospecific reagents. A non-cell exclusion agent is added to the separated bioentities to allow exclusion of non-nucleated components present in the sample. After purifying the target bioentity, it is then ready for analysis using a variety of different analysis platforms. Target bioentities include, without limitation, tumor cells, virally infected cells, fetal cells in maternal circulation, virus particles, bacterial cells, white blood cells, myocardial cells, epithelial cells, endothelial cells, proteins, hormones, DNA, and RNA. Target bioentities may be analyzed by a process selected from the group consisting of multiparameter flow cytometry, immunoflourescent microscopy, laser scanning cytometry, bright field base image analysis, capillary volumetry, manual cell analysis and automated cell analysis. Aggregation inhibiting agents suitable for use in the methods of the present invention, include, but are not limited to reducing agents, animal serum proteins, immune-complexes, carbohydrates, chelating agent, unconjugated ferrofluid, and diamino butane. In the case where the endogenous aggregation factor is of the IgM class and reactive with ferrofluids, preferred aggregation inhibiting agents are reducing agents, such as Mercapto ethane sulfonic acid [MES], Mercapto Propane Sulfonic acid [MPS] and dithiothreitol [DTT]. In a particularly preferred embodiment, the biospecific ligand is a monoclonal antibody having affinity for an epithelial cell adhesion molecule.

In an alternative and preferred embodiment of the invention, a method is provided for isolating target bioentities from a biological sample by controlling aggregation of magnetic nanoparticles. The method entails obtaining a biological specimen suspected of containing said target bioentity and contacting the biological specimen with a reagent effective to inactivate any endogenous aggregating factors present. Immunomagnetic suspensions are then prepared wherein the specimen is mixed with colloidal, magnetic particles coupled to a biospecific ligand having affinity for at least one antigen present on the target bioentity, the magnetic particles being further coupled to a first exogenous aggregation enhancing factor which comprises a first member of a specific binding pair. A second multivalent exogenous aggregation enhancing factor is then added to the immunomagnetic suspension to increase aggregation of the particles, the second aggregating enhancing factor comprising the second member of the specific binding pair, which reversibly binds to the magnetically labeled target bioentity. The sample is then subjected to a magnetic field to obtain a target bioentity enriched fraction. This preferred embodiment takes advantage of the fact that aggregating ferrofluid onto target entities in a controlled and reversible fashion results in substantially improved isolation efficiency.

In a further embodiment, the above described method further comprises the steps of adding at least one biospecific reagent which recognizes and labels at least one additional characteristic determinant on said target bioentity. The target bioentity so labeled is then separated in a magnetic field to remove unbound biospecific reagent. A non-cell exclusion agent is added to the separated bioentities to allow exclusion of non-nucleated components present in the sample. The target bioentity is then purified and further analyzed. In order to reverse the aggregation mediated by the exogenous aggregation factors, a member of the specific binding pair may be added in excess to the purified bioentity to reduce ferrofluid aggregation on the surface of cells, thereby facilitating viewing of the cells, e.g. in a microscope. Suitable specific binding pairs for this purpose include, without limitation, biotin-streptavidin, antigen-antibody, receptor-hormone, receptor-ligand, agonist-antagonist, lectin-carbohydrate, Protein A-antibody Fc, avidin-biotin, biotin analog-streptavidin, biotin analog-avidin, desthiobiotin-streptavidin, desthiobiotin-avidin, iminobiotin-streptavidin, and iminobiotin-avidin. Preferably, the biospecific ligand is a monoclonal antibody having affinity for epithelial cell adhesion molecule. Exemplary biospecific reagents include monoclonal antibodies, polyclonal antibodies, detectably labeled antibodies, antibody fragments, and single chain antibodies. Isolated target bioentities may be analyzed by a process selected from the group consisting of multiparameter flow cytometry, immunofluorescent microscopy, laser scanning cytometry, bright field base image analysis, capillary volumetry, manual cell analysis and automated cell analysis.

In accordance with the present invention, controlling aggregation of ferrofluid in a sample has several unexpected benefits previously noted, e.g. increasing efficiency of separation of some particular entity. It has been discovered that addition of an exogenous aggregation enhancing factor gives rise to increased magnetic loading, resulting in increased separation efficiency while reducing the amount of ferrofluid required to isolate the target bioentity. The increased magnetic loading also allows for reduced incubation periods and facilitates isolation of the target bioentity in the presence of a suboptimal magnetic field.

In an additional embodiment of the present invention a kit is provided which facilitates the practice of the methods described herein. An exemplary kit for isolating target bioentities includes i) coated magnetic nanoparticles comprising a magnetic core material, a protein base coating material, and an antibody that binds specifically to a first characteristic determinant of said target bioentity, said antibody being coupled, directly or indirectly, to said base coating material; ii) at least one antibody having binding specificity for a second characteristic determinant of said rare biological substance; iii) an aggregation inhibiting factor; and iv) a non-cell exclusion agent for excluding non-nucleated sample components other than said target bioentity from analysis.

A kit for improving the isolation efficiency of certain biological entities, such as might be required for isolating low antigen density tumor cells from a biological sample, is also provided in accordance with the present invention. This kit utilizes controlled and reversible aggregation of magnetic nanoparticles to achieve such improvement. Such a kit includes i) a reagent effective to inactivate endogenous aggregating factors; ii) coated magnetic nanoparticles comprising a magnetic core material, a protein base coating material, and an antibody that binds specifically to a first characteristic determinant of said tumor cell, the antibody being coupled, directly or indirectly, to the base coating material; the magnetic particles being further coupled to a first exogenous aggregation enhancing factor, the factor comprising one member of a specific binding pair; iii) at least one antibody having binding specificity for a second characteristic determinant of said tumor cell; iv) a second exogenous aggregation enhancing factor, the second aggregation enhancing factor comprising the second member of the specific binding pair; and v) a non-cell exclusion agent for excluding non-nucleated sample components other than the tumor cells from analysis. The kit may optionally include a reagent for reversing the exogenous aggregation factor. Specific binding pairs useful in such a kit, include without limitation, biotin-streptavidin, antigen-antibody, receptor-hormone, receptor-ligand, agonist-antagonist, lectin-carbohydrate, Protein A-antibody Fc, and avidin-biotin, biotin analog-avidin, desthiobiotin-streptavidin, desthiobiotin-avidin, iminobiotin-streptavidin, and iminobiotin-avidin. Reagents effective to inactivate endogenous aggregating factors include reducing agents, animal serum proteins, immune-complexes, carbohydrates, chelating agent, unconjugated ferrofluid, and diamino butane.

The methods, compositions and kits of the invention provide the means for controlling the aggregation of magnetic nanoparticles, thus facilitating the isolation, visualization and characterization of rare biological substances or cells from biological specimens.

BRIEF DESCRIPTION OF THE DRAWING

FIG. 1A, transmitted light only, low aggregation;

FIG. 1B, transmitted light only, high aggregation;

FIG. 1C, cells stained with Hoechst nuclear stain, low aggregation;

FIG. 1D, cells stained with Hoechst nuclear stain, high aggregation;

FIG. 1E, cells stained with the epithelial cell marker cytokeratin Alexa 488, low aggregation;

FIG. 1F, cells stained with the epithelial cell marker cytokeratin Alexa 488, high aggregation;

FIG. 1G, cells stained with tumor cell receptor marker erb2-conjugated to phycoerythrin, low aggregation;

FIG. 1H, cells stained with tumor cell receptor marker erb2-conjugated to phycoerythrin, high aggregation.

DETAILED DESCRIPTION OF THE INVENTION

Figure 1A:
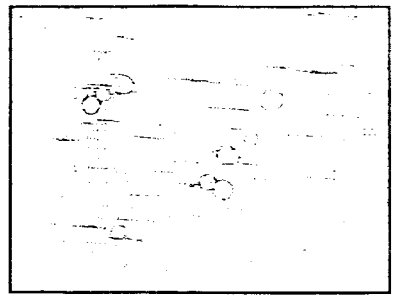
FIGS. 1A–1H are a series of micrographs depicting what is observed in a microscope in samples derived from blood donors with high levels of endogenous aggregating factors versus those with low levels of endogenous aggregation factors. Breast cancer cells were spiked into whole blood and selected using EPCAM colloidal magnetic particles and stained in suspension.
Figure 1B:
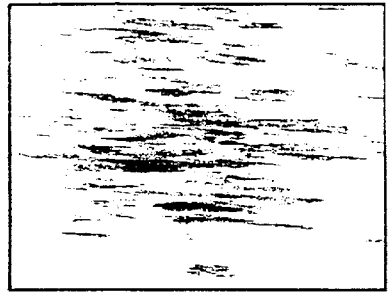
Figure 1C:
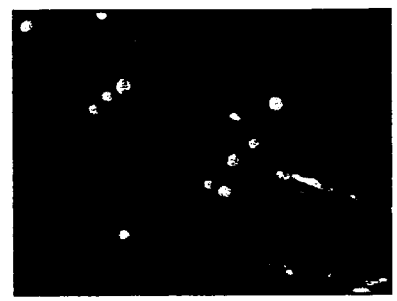
Figure 1D:
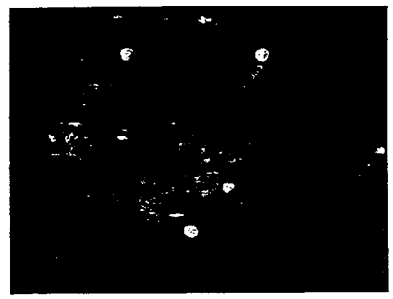
Figure 1E:
Figure 1F:
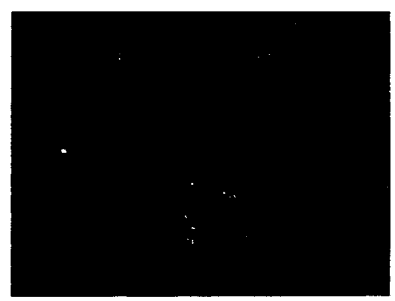
Figure 1G:
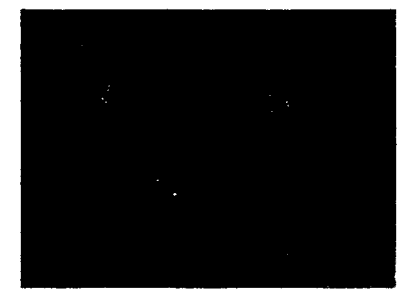
Figure 1H:

The term "target bioentities" as used herein refers to a wide variety of materials of biological or medical interest.

Examples include hormones, proteins, peptides, lectins, oligonucleotides, drugs, chemical substances, nucleic acid molecules, (e.g., RNA and/or DNA) and particulate analytes of biological origin, which include bioparticles such as cells, viruses, bacteria and the like. In a preferred embodiment of the invention, rare cells, such as fetal cells in maternal circulation, or circulating cancer cells may be efficiently isolated from non-target cells and/or other bioentities, using the compositions, methods and kits of the present invention. The term "biological specimen" includes, without limitation, cell-containing bodily, fluids, peripheral blood, tissue homogenates, nipple aspirates, and any other source of rare cells that is obtainable from a human subject. An exemplary tissue homogenate may be obtained from the sentinel node in a breast cancer patient. The term "determinant", when used in reference to any of the foregoing target bioentities, may be specifically bound by a biospecific ligand or a biospecific reagent, and refers to that portion of the target bioentity involved in, and responsible for, selective binding to a specific binding substance, the presence of which is required for selective binding to occur. In fundamental terms, determinants are molecular contact regions on target bioentities that are recognized by receptors in specific binding pair reactions. The term "specific binding pair" as used herein includes antigen-antibody, receptor-hormone, receptor-ligand, agonist-antagonist, lectin-carbohydrate, nucleic acid (RNA or DNA) hybridizing sequences, Fc receptor or mouse IgG-protein A, avidin-biotin, streptavidin-biotin and virus-receptor interactions. Various other determinant-specific binding substance combinations are contemplated for use in practicing the methods of this invention, such as will be apparent to those skilled in the art. The term "antibody" as used herein, includes immunoglobulins, monoclonal or polyclonal antibodies, immunoreactive immunoglobulin fragments, and single chain antibodies. Also contemplated for use in the invention are peptides, oligonucleotides or a combination thereof which specifically recognize determinants with specificity similar to traditionally generated antibodies. The term "detectably label" is used to herein to refer to any substance whose detection or measurement, either directly or indirectly, by physical or chemical means, is indicative of the presence of the target bioentity in the test sample. Representative examples of useful detectable labels, include, but are not limited to the following: molecules or ions directly or indirectly detectable based on light absorbance, fluorescence, reflectance, light scatter, phosphorescence, or luminescence properties; molecules or ions detectable by their radioactive properties; molecules or ions detectable by their nuclear magnetic resonance or paramagnetic properties. Included among the group of molecules indirectly detectable based on light absorbance or fluorescence, for example, are various enzymes which cause appropriate substrates to convert, e.g., from non-light absorbing to light absorbing molecules, or from non-fluorescent to fluorescent molecules. A nucleic acid dye or other reporter molecule, sometimes referred to herein as a non-cell exclusion agent, which is capable of identifying both target bioentities and certain non-target bioentities, such as intact nucleated cells, is added to the sample to allow exclusion of any residual non-nucleated cells or other potentially interfering sample components prior to analysis by flowcytometry, microscopy, or other analytical platforms. Non-cell exclusion agents may be reactive with DNA, RNA, protein, or lipids such that the amount of signal obtained is typical of that obtained for cells or the image obtained reveals typical features of a cell, such as cell and nuclear membranes, nucleus, and mitochondria.

The term "optimal" used herein describing ferrofluid concentration, magnetic field strength, or incubation time refers to the conditions used in a standard, unmodified assay, separation, isolation, or enrichment.

The term "sub-optimal" used herein describing ferrofluid concentration, magnetic field strength, or incubation time refers to the conditions used in an assay, separation, isolation, or enrichment which would produce inferior results, as compared to results obtainable under optimal conditions.

The term "ferrofluid" as used herein refers to magnetic nanoparticles in suspension. The terms ferrofluid and magnetic nanoparticles are used interchangeably herein.

Endogenous ferrofluid aggregation factors are those present in a sample isolated from a test subject. Exogenous aggregation factors are those provided herein which are added and/or reversed as desired by the investigator.

The preferred magnetic particles for use in this invention are particles that behave as colloids and are superparamagnetic. The colloids are characterized by their size, i.e., smaller than 200 nm or of a size which doesn't interfere with the analysis. The superparamagnetic particles become magnetic only when they are subjected to a magnetic field gradient and do not become permanently magnetic. The colloidal superparamagnetic particles do not separate or settle from aqueous solution for extended periods of time. These particles are composed of either single crystals of iron oxides or agglomerates of such crystals surrounded by molecules either physically adsorbed or covalently attached. The colloidal magnetic particles with the above characteristics can be prepared as described in U.S. Pat. Nos. 4,795,698; 5,512,332 and 5,597,531. A monoclonal antibody, which recognizes a specific subset of cells, conjugated to magnetic particles is preferred for use in this invention.

In the course of studies on rare cell isolation, a factor present in the blood of certain patients was discovered which effectuates aggregation of magnetic nanoparticles. Further, this enhanced aggregation effect appears to be readily reversible. Thus, rare cells having low receptor densities can be isolated more efficiently from moderately diluted whole blood in external field quadrupole or hexapole separators by "loading on" more ferrofluid than that which is specifically bound to a characteristic determinant of the rare cell of interest. When isolated cells are examined by microscopy, ferrofluid clusters are present on the cell membrane. Reversal of the enhancing effect deaggregates the clusters, facilitating microscopic analysis of the cells. This endogenous enhancing effect exists in varying levels in about 90% of apparently normal donor blood samples. By manipulating assay conditions, the resultant ferrofluid clusters can be dispersed without damaging the cells of interest. Thus, the present invention provides methods for eliminating the effects of endogenous ferrofluid aggregation factors and where desirable, means for constructing agents capable of controlled and reversible aggregation of ferrofluid. This permits effective and efficient isolation and enrichment and subsequent analysis of rare cells, and other biological entities such as viruses and bacteria.

The endogenous ferrofluid aggregating substance found in blood has the following characteristics: (1) it is present in plasma or serum; (2) it is sensitive to millimolar concentrations of dithiothreitol; and (3) it reacts with "bare" crystalline regions on direct coated ferrofluid, as described in U.S. Pat. No. 5,597,531. Control experiments revealed that the factor is not ferritin, transferrin, fibrinogen, C1q, human anti-mouse or anti-BSA antibodies. The aggregating substance is also not of the IgG subclass since IgG-depleted plasma also caused aggregation of the ferrofluid. Ferrofluid aggregation appears to be correlatable with ferrofluid or serum concentration. The dependency of aggregation on concentration of either component is similar to that observed with precipitin curves and based on the observations noted above, it was postulated that the substance is an IgM. This was conclusively proven by removing the IgM from the plasma samples via immunoaffinity purification. The resulting IgM depleted plasma did not effectuate ferrofluid aggregation.

Control experiments, where the same plasma samples were absorbed through a BSA affinity media, did show ferrofluid aggregation. Further study demonstrated that extensive adsorption of sera containing the aggregating factor with ferrofluids only removed a small amount of the total IgM and that purified human IgM causes ferrofluid aggregation. These observations along with identity studies of adsorbed aggregating factor and the ability to cause aggregation with adsorbed/desorbed material led to the conclusion that the aggregation factor in these experiments is, indeed, a highly specific IgM. Based on the inability to inhibit aggregation by any component used in forming the ferrofluid except for magnetite crystals poorly coated with protein or magnetite crystals partially coated with detergent, it is believed that the epitope recognized by the IgM is present on the magnetite crystalline surface. The role of this specific IgM is not known but it is present in a significant portion of the human population and at varying levels. It is possible that this antibody plays some role in iron metabolism.

Methods of manipulating endogenous enhancing factors are described herein which permit patient-to-patient comparison of isolated cells in a meaningful manner. Because the endogenous aggregation enhancing factor concentration varies in patient populations, it is difficult to create a standard procedure for separating rare circulating cells, be they tumor cells, fetal cells in maternal blood or virally infected cells. Recent discoveries in a co-pending application (Ser. No. 09/248,388) have demonstrated that the magnitude of the number of circulating cells is directly related to tumor burden and stage of disease in breast cancer patients. Similarly, viral burden has been shown to be of significance in the prognosis of HIV infection. The need for accurate quantitation of such entities is becoming ever more important. The methods disclosed herein are conveniently practiced by means of test kits which may be used to advantage in the clinical setting.

Having discovered the presence of this ferrofluid aggregation factor (FFAF) in donor sera, careful studies confirmed that its presence markedly improves the retrieval of spiked low density receptor tumor cells using monoclonal antibody conjugated ferrofluid. In these studies, cells spiked at levels of 1 cell/2 mls of blood containing FFAF are routinely retrieved at greater than 70% efficiency. In contrast, in donor blood where FFAF is absent, efficiency of retrieval is reduced to approximately 15–25%. From those experiments, the following observations were made:

1. low density receptor cells are often isolated less efficiently than cells with high density receptors;
2. separation efficiency varies considerably for low density receptor cells and this variation is dependent on the blood donor;
3. when either cell type (high or low density characteristic determinant cells) was examined via microscopy following ferrofluid/magnetic isolation from the blood of different donors, ferrofluid was aggregated in about 90% of patient samples; and
4. tumor cells retrieved had differing degrees of visible ferrofluid aggregated on their surfaces.

Moreover, since the aggregation material is sensitive to DTT, retrieved cells can be readily visualized by microscopy for morphological characteristics by reduction of the ferrofluid aggregates prior to observation.

In comparing the phenomena of FFAF and chaining (see U.S. Pat. No. 5,466,574) to enhance cell recoveries, some interesting conclusions can be drawn. When FFAF is present in blood in exceedingly low concentrations, as is the case in many individuals, excellent recoveries of low density receptor spiked cells are obtained, e.g., 1–5 cells/ml blood. The quality of the recovered cells, as assessed by the level of magnetic material on their surfaces is quite suitable for morphological examination or further manipulation. When FFAF is in high concentrations, recoveries are also excellent but the quality of the recovered cells is not acceptable as the agglomerates on the cells obscures their viewing. Hence, unlike the components of chaining, i.e. monoclonal antibody-ferrofluid "chains", which are limited by concentration, there is a level of FFAF which can lead to very effective cell separation, thus providing an isolated population of cells which can be studied effectively. In certain embodiments of the invention, endogenous FFAF's in the samples are inactivated at the outset so that aggregation can be controlled by the investigator by adding the compositions described herein. In this way, aggregation can be enhanced or inhibited as desired.

FFAF and any similar substances must be evaluated in assays to isolate rare cells. Such factors must be controlled in order to develop a test which functions reliably for every patient. For example, many individuals have anti-rodent antibodies, or antibodies to components, such as carbohydrates, which might be found on the surface of some magnetic nanoparticles. Other potential aggregating substances normally present in blood include C1q, rheumatoid factor, and blood clotting proteins. Such reactions must either be controlled, so as to make them constant from specimen to specimen, or be eliminated altogether. In the case of anti-rodent antibodies, this can be accomplished by adding rodent proteins to the system so as to inhibit their aggregating effects. This addition is quite different from adding such components to immunoassay systems. In the latter case, anti-rodent antibodies generally enhance isolation but also tend to increase false positives as they link captured antibody with labeling antibody in sandwich-type reactions. In contrast, additional antibodies used in the methods of the present invention enhance the recovery of low density receptor cells. Thus, in one case aggregating factors can artificially elevate false positives, and in another facilitate isolation of the target bioentity.

Besides competitively inhibiting such factors, they may be disabled or adsorbed from solution, or the determinant on the magnetic colloid to which such factors bind may be eliminated. FFAF activity may be inhibited by formulating a special buffer that contains optimal amounts of additives such as mouse and other animal serum proteins, immune-complexes, carbohydrates, chelating agents which inhibit various activation systems, including complement, and compounds which specifically inhibit the interaction of C1q with reacted antibody, such as diamino butane. In the case where FFAF is an IgM, reducing agents effectively disable the FFAF without affecting the ligands used for labeling cells. Thus, such factors could be selectively disabled chemically or enzymatically. Adsorption with appropriate materials, e.g., unconjugated ferrofluid, provides another route for removing aggregating factors from the sample.

It may also be possible to make the amount of aggregator constant from patient to patient so as to always have identical levels of enhancement. This may be accomplished in different ways. For example, all endogenous factors may be reduced to the same level in all patient samples. However this seems a difficult and impractical solution. As an alternative, a two step process may be employed where, as a first step, all endogenous FFAF's are disabled without affecting specific ligand binding of the ferrofluid to its target or subsequent cell analysis. The second step entails a controlled aggregation reaction. Colloidal magnetic materials conjugated to two kinds of ligands may be used to practice the two step method described above. One ligand, such as monoclonal antibody would be directed to cell surface determinants and effectively labels cells. The secondary ligand would have no reactivity with any component of blood yet have binding affinity for a multivalent component which would be added following binding of the primary ligand. Thus, additional magnetic colloid would bind to colloid already bound to cells, thereby enhancing their magnetic load just as FFAF does. Similarly, it would be preferable if the reaction of the secondary ligand and its multivalent component were reversible. By selecting the right components of the secondary reactions and their concentrations, it should be possible to add ferrofluid and the aggregation factor simultaneously.

Therefore, FFAFs are provided which facilitate controlled aggregation of ferrofluids, thereby enhancing recoveries of rarely occurring biological entities. The ideal aggregating factor is one which mediates a reversible aggregating effect. Reversal of aggregation eliminates magnetic nanoparticle clusters so as to facilitate visualization of isolated cells. The factors of the invention operate in a manner similar to the ideal magnetic particle conditions described above i.e., by converting colloid nanoparticles which are bound to target into large particles with the added ability to readily reverse that process. The identification and elucidation of an endogenous factor present in the blood of most normal donors which enhances the efficiency of isolation of low density receptor rare cells is described herein.

Preferable FFAFs include specific multivalent substances which recognize determinant(s) on ferrofluid magnetic particles thereby crosslinking the particles. This factor may naturally occur in plasma or may be an exogenously added reagent. Several types of exogenous reagents are suitable for this purpose and include, but are not limited to, IgG, dimeric IgG, IgM, Streptavidin, Avidin, Protein A, Protein G, dimeric or tetrameric poly-A or poly-T, or specific oligonucleotide sequences. The secondary ligand can be introduced onto ferrofluid and is recognized by FFAF. There are several types of secondary ligands which may be selected such as hapten, biotin, biotin analogues (iminobiotin, desthiobiotin), sheep IgG, goat IgG, rat IgG, poly-A or poly-T or oligonucleotide. FFAF-secondary ligand interaction may be either reversible or irreversible but a reversible interaction is preferred. There are several reagents which may be used to reverse FFAF-secondary ligand interaction such as reducing agents, excess of haptens, excess of hapten analogues, excess of analogues of the secondary reagent, change of salt concentration, change of pH or change of temperature.

When an assay or separation is performed under optimal conditions, the percent recovery of the target cells is maximized. However, the ability to modify the conditions is apparent when exogenous aggregation is target cells, the amount of ferrofluid needed for maximum recovery is quite high without exogenous aggregation, to ensure that each target is magnetically responsive by saturating all the available binding sites. One benefit of this invention is that less total ferrofluid is needed for separation, as it does not need to saturate all the available binding sites. This is due to the ability to form crosslinks of magnetic particles, mediated by the exogenous aggregation factor and increase the magnetic mass per binding site. Instead of rendering cells magnetically responsive by the use of many single magnetic particles per cell, i.e. one particle binds one cell surface antigen, the aggregates of multiple particles can bind the single antigen and will maintain the same magnetic force as optimally captured cells. Each particle now has the capability to bind a cell surface antigen or another particle. In other words, even though less total ferrofluid is used, each target cell will have the same magnetic responsiveness, and the resulting separation efficiency will be comparable to that obtained under optimal conditions. Optimally, 10 $\mu$g of ferrofluid is used per 1 ml of sample. This concentration may be reduced 10-fold in accordance with the present invention.

In addition to reducing the amount of ferrofluid needed, the magnetic strength as well as the incubation time can be reduced. Because the aggregates of the invention are larger than individual magnetic particles in a non-aggregating separation, a lesser magnetic field strength can still move the aggregates. Promoting exogenous aggregation creates temporary and reversible large magnetic particles from small magnetic particles. Indeed, the benefits of large particles, including the ability to use weak magnetic fields for separation, can be applied to the present invention. The quadrupole magnetic separators typically used maintain a field gradient strength of 6.3 kGauss/cm at the vessel surface. Magnetic arrangements, such as dipoles, which have almost half the magnetic field strength at the vessel surface may be utilized in practicing the methods of the present invention.

In the non-aggregating system, longer incubation times are required to increase the number of magnetic particles per cell for effective separation. In this system, one magnetic particle will bind one cell surface antigen. However, in an exogenously-induced aggregation system, the same number of particles per cell can be achieved by causing multiple particles per antigen, via the induced aggregates. This allows the incubation time to be shortened because not all of the available binding sites will need to be bound to magnetic particles. By adding this second binding pair member, the particles now can bind to other particles, instead of only being capable of binding to free cell surface antigens. Therefore, as explained above, the binding sites do not need to be saturated to have the same magnetic responsiveness as optimal conditions, which allows the reduction of incubation time. The minimum time for magnetic incubations is 30 minutes. Using the present invention, these times may be reduced up to 3-fold. However, it is not intended that both ferrofluid concentration be reduced and incubation time be shortened simultaneously. Variations of these steps should be exploited independently of one another in order to maintain maximal recovery of target bioentities.

A secondary ligand which is recognized by an exogenous ferrofluid aggregation factor will be coupled to ferrofluid in addition to the above monoclonal antibody by standard coupling chemistry. The secondary ligand may be a small molecule such as hapten or biotin analogue or a big molecule such as an antibody or a specific protein or a polymer such as polypeptides or polyoligonucleotides. A biotin analogue such as desthiobiotin is preferred for conjugation to magnetic particles as a secondary ligand in this invention as it exhibits a lower affinity ($Ka=10^6$ $M^{-1}$ for streptavidin, as compared to native biotin ($Ka=10^{15}$ $M^{-1}$). The interaction between streptavidin and desthiobiotin can be easily disrupted by the addition of excess biotin. The combination of desthiobiotin and avidin has been used to remove magnetic particles or insoluble phase from the target substances (PCT/US94/10124 and U.S. Pat. No. 5,332,679). In this invention, that combination is used only to aggregate and disaggregate magnetic particles and not to remove magnetic particles from the target substance.

The reaction vessel for use in this invention may be either glass or plastic, however, plastic tubes are preferred. The bottom of the tube may be round or conical in shape. Tubes with different lengths or diameters may be used to process different volumes of samples. For example, in some instances a 50 ml conical tube may be used to process 20 ml of blood or more. In one embodiment of this invention, a 12×75 mm polystyrene tube or 15 ml conical tube is used. The reaction vessel used during incubation with magnetic particles and the vessel used during magnetic separation does not necessarily need to be the same. Two different types of vessels may be used, one type for incubation and another type for magnetic separation. However, it is preferred to use only one vessel in both cases. The magnetic separation vessel may be a tube or a flow-through chamber or some other device.

The test medium used in practicing the present invention may be any liquid or solution which contains the target substance and is preferably blood. A test sample in the reaction vessel is incubated with a ferrofluid conjugated to antibodies specific for a target substance and a secondary ligand specific for FFAF. Additionally, an exogenous FFAF is added simultaneously with ferrofluid to the test sample or after binding of ferrofluid to target substance. Optionally, a reagent which inhibits or disables naturally occurring aggregating factor may be added simultaneously with ferrofluid, or added prior to ferrofluid addition. After an optimum incubation time, magnetically labeled targets are separated from the rest of the test medium in a magnetic separator. The magnetic separator and separation time are selected based upon test medium and reaction vessel. It is preferred to use high-gradient magnetic separation devices such as those described in U.S. Pat. No. 5,186,827. After aspirating the uncollected liquid, the collected cells may be resuspended in an isotonic buffer or permeabilizing solution to permeabilize cells for intracellular staining. The magnetically labeled cells are reseparated magnetically to remove permeabilizing reagents. The collected cells are resuspended in a small volume of cell buffer for staining with labeling substances. The volume of the buffer may be from 100–300 µl. Optionally the cell buffer may contain staining antibodies. Additionally, the cell buffer may contain a disaggregating reagent as described above, e.g., biotin. The final concentration of biotin may be from 1–5 mM. The incubation time for antibody staining or for ferrofluid disaggregation with disaggregating reagent may be from 10–60 minutes and is preferably 15 minutes. After optimum staining with antibodies or disaggregation of ferrofluid, excess reagents may be removed from cells by another magnetic separation. After aspirating the uncollected liquid, the collected cells are resuspended in a small volume of isotonic buffer. The volume of this buffer may be from 100–500 µl. The ferrofluid labeled cells may be further processed or analyzed by flowcytometry or microscopy.

While magnetic particles conjugated to antibody only have been described above, other types of conjugated magnetic particles are contemplated for use in the present invention. Magnetic particles conjugated to proteins other than antibodies may be used. For example, streptavidin conjugated magnetic particles may be used to bind target cells which are labeled with antibody-biotin conjugates. Following labeling of target cells, excess unbound antibody-biotin may be removed by a wash step using a centrifuge. The target cells labeled with antibody-biotin are then incubated with streptavidin ferrofluid for magnetic labeling of cells. Desthiobiotin conjugated to any polymer or protein (aggregating factor) will be added to the test medium to aggregate ferrofluid. Aggregating factor may be added simultaneously with magnetic particles or after the magnetic particles bind the target cells. The number of desthiobiotins per polymer or protein should be more than one to aggregate ferrofluid. Preferably desthiobiotin conjugated to bovine serum albumin (BSA) may be used. The number of desthiobiotins on BSA may be 2–10. Such desthiobiotin/protein conjugates may be synthesized as set forth hereinbelow.

Although the present invention is described herein primarily with reference to tumor cell selection from blood, the invention is not limited to tumor cell selection. Other cell types present in blood, leukophoresis or bone marrow, such as CD34, CD4, and fetal cells may be selected. The antigenic determinants on those cells may be low to high. More generally, the invention applies to the isolation of any cell which requires magnetic enhancement for its efficient isolation.

The following examples are provided to illustrate various embodiments of the invention. These examples are not intended to limit the scope of the invention in any way.

EXAMPLE I

The following data illustrate the effects of the FFAF of the present invention on the recovery of low and high density receptor tumor cells spiked into blood samples. An exemplary FFAF has been identified as a specific IgM present in the blood samples of most donors. Reducing agents such as dithiothreitol (DTT) and mercaptoethane sulfonic acid (MES) which cleave disulfide linkages, prevented ferrofluid aggregation in blood by converting pentameric IgM to its monomeric form. DTT is not a preferred reagent for use in the methods of the present invention, as high concentrations alter cellular morphology, and are toxic to target cells and leukocytes.

In this example, the effect of MES on ferrofluid aggregation and tumor cell recovery of both high and low antigen density tumor cells from spiked blood is described. The protocol used for this study was as follows. Blood (2 ml) was placed in a 12×75 mm polystyrene tube and 1 ml of Immunicon dilution-wash buffer was added to dilute the blood. Next, 100 µl of cell buffer (isotonic 7 mM phosphate, pH 7.4 with 1% BSA and 50 mM EDTA) containing approximately 1000 SKBR3 or PC3 cells was added. Increasing volumes of MES (not exceeding 150 µl) were added to the blood samples to obtain different concentrations of reducing agent. After mixing, EpCAM MAb (GA73.3; 50 µl) conjugated ferrofluid magnetic particles were added to the sample. The final concentration of magnetic particles was 5 µg/ml. The blood sample was mixed well and incubated for 15 minutes at room temperature. After the incubation, the tube containing the blood sample was placed in a quadrupole magnetic separation device. Magnetic separation was performed for 10 minutes. The supernatant was aspirated and the tube was removed from the magnetic device. The magnetically collected cells were resuspended in 1 ml of dilution-wash buffer and reseparated in a quadrupole magnetic separation device for 5 minutes. The supernatant was discarded and after removal from the quadrupole device, the target cells were resuspended in 150 µl of dilution wash buffer. A portion of this sample (5 µl) was spotted on a microscope slide. The recovered cells were then photographed using a microscope with a digital camera attached to it.

The remaining sample was subjected to flowcytometry analysis to assess the recovery of tumor cells using the following procedure. Phycoerythrin (PE)-conjugated MAb (5 µl) specific for tumor cells (Neu 24.7) and 5 µl of peridinin chlorophyll protein (PerCP)-conjugated CD45 monoclonal antibody were added to the sample which was then incubated for 15 minutes. After the incubation, 1 ml of dilution-wash buffer was added and a magnetic separation was performed in order to remove excess staining antibodies. The magnetically collected cells were resuspended in 500 µl of dilution-wash buffer. Nucleic acid dye (10 µl) and 5 µl of 3 mM sized fluorescent beads (5000) were added to this sample. The sample was then analyzed on a FACSCalibur flowcytometer (Becton Dickinson) using FL1 as threshold. The fraction of the fluorescent beads acquired in the flowcytometer was used to determine the amount of sample analyzed by flowcytometry which, in turn, facilitates calculation of the recovery of spiked tumor cells.

| Concentration of MES (mM) | Recovery of tumor cells (%) | |
|---|---|---|
| | SKBR3 | PC3 |
| 0 | 77 | 46 |
| 20 | 80 | 50 |
| 50 | 80 | 31 |
| 75 | 82 | 27 |
| 100 | 70 | 17 |

When viewed by microscopy, the final sample showed free ferrofluid aggregates and ferrofluid aggregates on tumor cells in the absence of MES. As the concentration of MES was increased, ferrofluid aggregates decreased and no aggregates were seen at higher concentrations of MES. These visual results were then compared with tumor cell recovery as measured by flowcytometry. The addition of MES had no significant effect on recovery of SKBR3 cells (high antigen density) although microscopy revealed that it decreased ferrofluid aggregation in solution and on cell surfaces. In contrast, MES had a significant effect on the recovery of PC3 cells (low antigen density). As the concentration of MES was increased from 0–100 mM, recovery was decreased from 47% to 17%. This decrease in recovery of PC3 cells in the presence of increasing concentrations of MES was due to inhibition of ferrofluid aggregation and not due to any side effects of MES on cells, as MES did not decrease the recovery of same spiked PC3 cells from lysed blood samples. Lysed blood is obtained by lysing red blood cells with ammonium chloride followed by wash step which removes plasma and ammonium chloride. Lysed blood samples contain only leukocytes (white cells) whereas whole blood also contains erthyrocytes and plasma. No ferrofluid aggregation is observed with lysed blood. Moreover, MES has no significant effect on cell morphology. These data show that low antigen density cells were isolated less efficiently than high antigen density cells and inhibition of ferrofluid aggregation dramatically affects the isolation of low antigen density cells. Ferrofluid aggregation was also not observed when washed blood (blood cells with plasma removed) samples were utilized Therefore, washed blood samples were used as a control for no aggregation. Just as with whole blood, the recovery of SKBR3 cells was not decreased with washed blood. PC3 cell recovery on the other hand was decreased significantly (2 to 5-fold) when washed blood was used. This data clearly shows that ferrofluid aggregation does not have any effect on SKBR3 cells recovery but has a major effect on PC3 cells recovery.

In summary, aggregation of tumor specific ferrofluid with the plasma component (IgM) present in blood of many patients at varying levels has a significant effect on recovery of low antigen density cells. Recovery of such cells is affected by the extent of ferrofluid aggregation and increases with increasing aggregation. Ferrofluid aggregation increases the recovery of low antigen density cells by increasing magnetic load on the cells. Ferrofluid aggregation can vary from one blood donor to another depending upon the concentration of the aggregating factor or aggregator. As a result, the recovery of tumor cells will vary from person to person even though they may possess the same number of circulating tumor cells. It is also possible that the concentration of the aggregator present in the blood from the same person can vary with time thus altering the extent of ferrofluid aggregation and recovery of tumor cells. The best way to prevent this variation is to prevent naturally occurring ferrofluid aggregation. However, this gives rise to a decrease in the efficiency of tumor cells isolation and detection. One means to increase tumor cell recovery under these circumstances will be to improve the magnetic device with a higher gradient which can pull weakly magnetic labeled cells effectively and increase their recovery. The other way to increase the recovery of tumor cells will be to mimic natural ferrofluid aggregation with an exogenous reagent. This reagent can be a specific multivalent reagent which can recognize ferrofluid and can be added to the blood and ferrofluid. The specific reagent will aggregate ferrofluid similarly to IgM but under a controlled reaction. Controlled aggregation will have two advantages: (1) the percentage of tumor cells recovered will increase; and (2) the percentage of tumor cells recovered will not vary from patient to patient and will not vary with time from the same patient when the samples have the same number of tumor cells.

EXAMPLE II

Preparation of Desthiobiotin/EpCAM MAb Ferrofluid for Controlled Aggregation

A base ferrofluid was made as described in U.S. Pat. No. 5,698,271. Monoclonal antibody to the epithelial cell adhesion molecule (EpCAM) was conjugated to base material by standard coupling chemistry, as used in U.S. patent application Ser. No. 09/248,388. EpCAM MAb ferrofluid was then resuspended in 20 mM HEPES, pH 7.5 for conjugation to desthiobiotin using N-hydroxysuccinimide-DL-desthiobiotin (NHS-desthiobiotin) (Sigma, Cat.# H-2134). A stock solution of NHS-desthiobiotin was made in DMSO at 1 mg/ml. NHS-desthiobiotin (19 µg) was added to 1 mg of EpCAM MAb ferrofluid and incubated at room temperature for 2 hours. Unreacted NHS-desthiobiotin was removed by washing 3 times with 20 mM HEPES, pH 7.5 containing 1 mg/ml BSA, 0.05% ProClin 300 using a high gradient magnet. After the final wash, desthiobiotin/EpCAM MAb ferrofluid was resuspended in Immunicon ferrofluid storage buffer and filtered through a 0.2 µm syringe filter.

EXAMPLE III

Increase of Recovery of Low Antigen Density PC3 Tumor Cells from Spiked Blood by Aggregation of Desthiobiotin/EpCAM Ferrofluid with Streptavidin In this example, prostate carcinoma cells (PC3) which have a low EpCAM antigen density were spiked into normal blood and used as a model system to assess recovery of those spiked cells. A known number of PC3 cells (~5000) in 50 μl of buffer (isotonic 7 mM phosphate, pH 7.4 with 1% BSA and 50 mM EDTA) were spiked into 1 ml of normal blood without plasma in a 12×75 mm polystyrene tube. Blood without plasma was used in these experiments to prevent any interference of plasma components in the selection of target cells and it was prepared by centrifugation of blood. 500 μl of Immunicon dilution-wash buffer and 15 μl of streptavidin at different concentrations in PBS were added to aliquots of the blood sample. After mixing the sample, desthiobiotin/EpCAM MAb ferrofluid (25 μl) from Example 1 was added to the sample, mixed well and incubated at room temperature for 15 minutes. The final concentration of ferrofluid was 5 μg/ml. After the incubation, the tube containing the blood sample was placed in a quadrupole magnetic separator for 10 minutes for collection of magnetically labeled cells. The uncollected sample was aspirated and the tube was removed from the magnetic separator. The magnetically collected cells were resuspended in 750 μl of dilution-wash buffer and reseparated in a magnetic separator for 5 minutes. The uncollected sample was discarded again and the collected cells were resuspended in 150 μl of dilution-wash buffer after removal of the tube from the magnetic separator.

The sample was then stained with antibodies to determine the recovery of tumor cells by flowcytometry as follows. 5 μl of phycoerythrin (PE)-conjugated MAb specific for tumor cells (Neu 24.7) and 5 μl of peridinin chlorophyll protein (PerCP)-conjugated CD45 MAb were added to the sample and incubated for 15 minutes. After the incubation, 1 ml of dilution-wash buffer was added and a magnetic separation was performed for 5 minutes in order to remove excess staining antibodies. The magnetically collected cells were resuspended in 500 μl of dilution-wash buffer. Nucleic acid dye (10 μl) and 5 μl of 3 μM fluorescent beads (5000) were added to this sample. The sample was then analyzed on a FACSCalibur flowcytometer (Becton Dickinson) using FL1 as threshold. The fraction of the fluorescent beads acquired in the flowcytometer was used to determine the amount of sample analyzed by flowcytometry which was then used to calculate the recovery of spiked tumor cells. The percent recovery of tumor cells are shown in the following Table.

| Concentration of Aggregator, Streptavidin (μg/ml) | Tumor Cells (PC3) % recovery |
| --- | --- |
| 0.0 | 14 |
| 0.2 | 60 |
| 0.5 | 74 |
| 2.0 | 80 |
| 5.0 | 75 |

The samples which were left after the flowcytometry analysis were divided into two parts. Biotin from a stock solution in PBS was added to one part of the sample to final concentration of 2 mM and incubated at room temperature for 15 minutes to disaggregate streptavidin-mediated ferrofluid aggregates. These samples (5 μl) were spotted on a microscope slide and photographs of the recovered cells were taken using a microscope with a digital camera attached to it. The data indicate that the recovery of tumor cells (PC3) was increased significantly as the concentration of aggregator (streptavidin) was increased, reaching a maximum at a 2 μg/ml concentration of streptavidin. These results were correlated to free ferrofluid aggregates in solution and ferrofluid aggregates on cells as observed with microscopy. There were no ferrofluid aggregates at 0 μg/ml of streptavidin and ferrofluid aggregates were increased as the concentration of streptavidin was increased. Streptavidin causes aggregation of ferrofluid by multivalent binding of streptavidin to desthiobiotin on different ferrofluid particles. All these ferrofluid aggregates were reversibly disaggregated by the addition of excess biotin. The principle of this disaggregation of ferrofluid by excess biotin was due to displacement of desthiobiotin from streptavidin as biotin has a higher affinity than desthiobiotin for streptavidin.

EXAMPLE IV

Recovery of Spiked Low and High EpCAM Antigen Density Cells from Blood With and Without Aggregation of Desthiobiotin/EpCAM MAb Ferrofluid Breast carcinoma cells (SKBR3) have about 7-times higher EpCAM antigen density compared to PC3 cells and were chosen as the model high antigen density tumor cells for this example. A known number of SKBR3 or PC3 cells in cell buffer were spiked into 1 ml of blood without plasma separately in a 12×75 mm tube. Ferrofluid dilution-wash buffer (500 μl) and 15 μl of PBS containing streptavidin were added to the sample. After mixing the sample, 25 μl of desthiobiotin/EpCAM MAb ferrofluid was added and the blood sample mixed well and incubated for 15 minutes. After incubation, the tube was placed in a quadrupole magnetic separator for 10 minutes to collect magnetically labeled cells. The magnetically isolated cells were analyzed for recovery of tumor cells by flowcytometry and for observation of cells by microscopy as described in Example II.

| Concentration of aggregator, Streptavidin (μg/ml) | PC3 cells recovery (%) | SKBR3 cells recovery (%) |
| --- | --- | --- |
| 0 | 23 | 91 |
| 2 | 77 | 98 |

The data reveal a significant difference in recovery of tumor cells between low and high antigen density cells when the ferrofluid aggregator, streptavidin, was not added to the blood sample. There were also no ferrofluid aggregates in solution or on cell surfaces without streptavidin as observed with microscopy. Addition of streptavidin to the blood sample increased the recovery of low antigen density PC3 cells significantly (3-fold) with a commensurate increase of ferrofluid aggregation in solution and on the cells. On the other hand, there was only a small difference in recovery of high antigen density SKBR3 cells with and without streptavidin present in the blood sample. There were enough ferrofluid particles on SKBR3 cells even without ferrofluid aggregation to collect them effectively and to recover all of them. Ferrofluid aggregates in solution and on cells were completely disaggregated by the addition of excess biotin to the sample. In the case of low antigen density cells, there were not enough ferrofluid particles on cells to be collected effectively by magnetic methods. Ferrofluid aggregation by streptavidin increased the number of particles on these cells facilitating collection, effectively resulting higher recovery. It is also noteworthy that aggregation of ferrofluid increased the recovery of low antigen density cells close to that obtained with the high antigen density cells. In other words, there was no significant difference in recovery of low and high antigen density tumor cells upon addition of reversible ferrofluid aggregator to the blood sample.

EXAMPLE V

Inhibition of Ferrofluid Aggregation by Endogenous Aggregation Factors and Creation of Controlled Ferrofluid Aggregation With an Exogenous Aggregation Factor In this example, a method is provided to inhibit all endogenous ferrofluid aggregation factors and to create controlled ferrofluid aggregation by addition of an exogenous aggregation factor. The endogenous ferrofluid aggregation factors present in the sample can be inhibited by adding a variety of inhibitors to the sample. These inhibitors will act on different endogenous aggregation factors and prevent them from either crosslinking or binding to ferrofluid to cause aggregation. Inhibition will eliminate any variations in ferrofluid aggregation from sample to sample as endogenous aggregation factors are present at different concentrations in different samples. Once endogenous factor-ferrofluid aggregation is prevented, ferrofluid aggregation can be promoted by adding an exogenous aggregation factor which can enhance the recovery of targets efficiently. The exogenous aggregation can be controlled consistently with all the samples and it can be readily reversed.

The blood sample is preincubated with a buffer containing inhibitors to inhibit endogenous ferrofluid aggregation factors before ferrofluid is added to the blood. The antibody coupled ferrofluid contains bovine serum albumin and streptavidin on the surface of ferrofluid particles in addition to antibody. Therefore, the possible ferrofluid aggregation factors can be IgM (specific for crystal surface), human-anti-mouse antibody (HAMA), human-anti-bovine serum albumin antibody (HABAA), human-anti-streptavidin etc. If any of the above aggregation factors are present in plasma, they will recognize and bind to ferrofluid and cause ferrofluid to aggregate. It is already known that some patient plasma samples have HAMA and HABAA present therein. Clearly, any other components used to manufacture ferrofluids could also be targets for aggregation and would needs to be dealt with accordingly.

One of the inhibitors can be a reducing agent, such as mercaptoethane sulfonic acid at 100 mM, which can disable IgM-induced aggregation without affecting the ligands used for labeling cells. The reducing agent can be added as a single reagent to the blood or could be placed in a blood collection tube. The second inhibitor can be bovine serum albumin, which can be included in the buffer at 10 mg/ml, and will neutralize any HABAA. The third inhibitor can be nonspecific mouse antibody, in particular, the appropriate isotype which matches the antibody on the ferrofluid. This can be included in the buffer at a concentration of 0.5–5 mg/ml to neutralize even the most severe HAMA. The fourth inhibitor can be Streptavidin to be included in the buffer, if necessary, to neutralize any anti-streptavidin antibody present in plasma. However, there is no any information regarding the existence of anti-streptavidin antibody in plasma at this date.

The pre-treatment of blood with the above buffer and reducing agent can be from 15–30 minutes to neutralize all endogenous aggregation factors. After all endogenous aggregation factors are neutralized, an exogenous ferrofluid aggregation factor is added to the sample, followed by ferrofluid. The ferrofluid is coupled to an antibody specific for targets, as well as to another ligand specific for the exogenous aggregation factor. After optimum labeling of target cells with ferrofluid and induced aggregation of ferrofluid with exogenous aggregation factor, the sample is subjected to magnetic separation to enrich targets. After removing all non-targets, magnetically-labeled targets and free ferrofluid are resuspended in a small volume of buffer. The magnetically-labeled targets, such as cells, can be permeabilized to stain intracellular antigens. The sample is then incubated with different staining reagents depending upon the desired analysis method, including flow cytometry or fluorescent or bright field microscopy. After optimum incubation time, the excess staining reagents are removed by wash step using magnetic separation. The magnetically-labeled cells are then resuspended in a small volume of buffer. The final sample contains free ferrofluid aggregates and aggregates on target cells. The final sample without any further treatment can be used for flowcytometry analysis, as ferrofluid aggregation on cell surface does not interfere with the analysis. However, ferrofluid aggregation on cell surface interferes with microscopy analysis. In such cases, exogenous mediated-ferrofluid aggregation should be reversed. This can be achieved by resuspending the final sample in a buffer containing a disaggregation factor which binds to exogenous aggregation factor. The disaggregation factor disaggregates all ferrofluid aggregates, leaving cells easy to view and analyze. These methods permit effective target recovery and visualization for morphology studies.

Several patents and pending U.S. patent applications are referred to in the present specification. The entire disclosures of each of these patents and patent applications are incorporated by reference herein.

While certain of the preferred embodiments of the present invention have been described and specifically exemplified above, it is not intended that the invention be limited to such embodiments. Various modifications may be made thereto without departing from the scope and spirit of the invention, as set forth in the claims.

What is claimed is:

1. A method for isolating a target bioentity from a biological sample by means of colloidal magnetic particles, comprising:

a) obtaining a biological sample suspected of containing said target bioentity together with non-target bioentities and endogenous aggregating factors;

b) contacting said biological sample with a reagent effective to inactivate any endogenous aggregating factors present in said sample without adversely affecting cellular morphology;

c) preparing an immunomagnetic suspension comprising a mixture of said sample and colloidal, magnetic particles coupled to a biospecific ligand having binding affinity for at least one characteristic determinant present on said target bioentity; and d) subjecting said immunomagnetic suspension to a magnetic field to obtain a target bioentity-enriched fraction.

2. A method as claimed in claim 1, further comprising the steps of e) purifying said target bioentity from said enriched fraction; and f) analyzing said purified target bioentity.

3. A method as claimed in claim 2, wherein said target bioentities are analyzed by a process selected from the group consisting of multiparameter flow cytometry, immunofluorescent microscopy, laser scanning cytometry, bright field base image analysis, capillary volumetry, manual cell analysis and automated cell analysis.

4. A method as claimed in claim 1, further comprising the steps of:
   e) adding to said target bioentity enriched fraction at least one biospecific reagent which has binding affinity for at least one additional characteristic determinant on said target bioentity;
   f) separating said target bioentity in a magnetic field to remove unbound biospecific reagent from said enriched fraction.

5. A method as claimed in claim 4, further comprising the steps of:
   g) purifying said separated target bioentity; and
   h) analyzing said purified target bioentity.

6. A method as claimed in claim 4, further comprising the steps of:
   g) adding a non-cell exclusion agent to said separated target bioentities to allow exclusion of non-nucleated entities present in the sample;
   h) purifying said target bioentity; and
   i) analyzing said purified target bioentities.

7. A method as claimed in claim 6, wherein said reagent effective to inactivate any endogenous aggregating factors is a reducing agent selected from the group consisting of mercapto ethane sulfonic acid, mercapto propane sulfonic acid and dithiothreitol.

8. A method as claimed in claim 7, wherein said biospecific ligand is a monoclonal antibody having affinity for epithelial cell adhesion molecule.

9. A method as claimed in claim 1, wherein said target bioentity is selected from the group consisting of tumor cells, virally infected cells, fetal cells in maternal circulation, virus particles, bacterial cells, white blood cells, myocardial cells, epithelial cells, endothelial cells, proteins, hormones, DNA, and RNA.

10. A method as claimed in claim 1, said reagent being at least one selected from the group consisting of a reducing agent, an animal serum protein, an immune-complex, a carbohydrate, a chelating agent, an unconjugated ferrofluid, and diamino butane.

11. A method as claimed in claim 1, wherein said biospecific ligand is a monoclonal antibody.

12. A method for isolating target bioentities from a biological sample by means of colloidal magnetic particles, comprising:
   a) obtaining a biological sample suspected of containing said target bioentities together with non-target bioentities and endogenous aggregating factors;
   b) contacting said biological sample with a reagent effective to inactivate any endogenous aggregating factors present in said sample without adversely affecting cellular morphology;
   c) preparing an immunomagnetic suspension comprising a mixture of colloidal, magnetic particles coupled to a biospecific ligand having affinity for at least one characteristic determinant present on said target bioentity, said magnetic particles being further coupled to a first exogenous aggregation enhancing factor which comprises one member of a specific binding pair;
   d) adding a second exogenous aggregation enhancing factor to said immunomagnetic suspension to increase aggregation of said particles, said second aggregating enhancing factor comprising the other member of said specific binding pair; and
   e) subjecting said sample to a magnetic field to obtain a target bioentity-enriched fraction.

13. A method as claimed in claim 12, further comprising the steps of:
   f) adding to said immunomagnetic suspension at least one biospecific reagent having binding affinity for at least one additional characteristic determinant on said target bioentity;
   g) separating said target bioentities in a magnetic field to remove unbound biospecific reagent; and
   h) adding a non-cell exclusion agent to said separated bioentities to allow exclusion of non-nucleated entities present in the sample;
   i) purifying said target bioentities; and
   j) analyzing said separated and purified target bioentities.

14. A method as claimed in claim 12, further comprising examining said purified target bioentity-enriched fraction to determine the degree of aggregation mediated by said first and second members of said specific binding pair.

15. A method as claimed in claim 12, wherein one or the other member of said specific binding pair is added to said purified bioentity fraction to reverse aggregation of said sample, thereby facilitating analysis of said target bioentities.

16. A method as claimed in claim 12, wherein said specific binding pair is selected from the group consisting of biotin-streptavidin, antigen-antibody, receptor-hormone, receptor-ligand, agonist-antagonist, lectin-carbohydrate, Protein A-antibody Fc, and avidin-biotin, biotin analog-streptavidin, biotin analog-avidin, desthiobiotin-streptavidin, desthiobiotin-avidin, iminobiotin-streptavidin, and iminobiotin-avidin.

17. A method as claimed in claim 12, wherein said biospecific ligand is a monoclonal antibody.

18. A method as claimed in claim 17, wherein said biospecific ligand is an antibody having affinity for epithelial cell adhesion molecule.

19. A method as claimed in claim 12 wherein said at least one biospecific reagent is selected from the group of consisting of monoclonal antibodies, polyclonal antibodies, detectably labeled antibodies, antibody fragments, and single chain antibodies.

20. A method as claimed in claim 12 wherein said target bioentities are analyzed by a process selected from the group consisting of multiparameter flow cytometry, immunofluorescent microscopy, laser scanning cytometry, bright field base image analysis, capillary volumetry, manual cell analysis and automated cell analysis.

21. A method as claimed in claim 12, wherein said immunomagnetic suspension is incubated for less than 30 minutes.

22. A method as claimed in claim 12, wherein said purification of said sample is performed in a magnetic field gradient of less than 6.3 kGauss/cm.

23. A method as claimed in claim 12, wherein said colloidal magnetic particle concentration in said immunomagnetic suspension is less than 10 µg per milliliter.

24. A method for isolating low antigen density tumor cells from a biological sample by means of colloidal magnetic particles, comprising:
   a) obtaining a biological sample suspected of containing said tumor cells together with non-tumor cells and endogenous aggregating factors;
   b) preparing an immunomagnetic suspension comprising a mixture of said sample and colloidal, magnetic particles coupled to a biospecific ligand having affinity for at least one characteristic determinant present on said tumor cell, said magnetic particles being further coupled to a first exogenous aggregation enhancing factor, said factor comprising one member of a specific binding pair;

c) adding a second exogenous aggregation enhancing factor to said immunomagnetic suspension to increase aggregation of said particles, said second aggregating enhancing factor comprising the other member of said specific binding pair; and d) purifying said sample in a magnetic field to obtain a tumor cell-enriched fraction.

25. A method as claimed in claim 24, further comprising the steps of:

e) adding to said fraction, at least one biospecific reagent having binding affinity for at least one additional characteristic determinant on said tumor cell;

f) separating said tumor cells in a magnetic field to remove unbound biospecific reagent;

g) adding a non-cell exclusion agent to said separated cells to allow exclusion of non-nucleated entities present in the sample; and h) analyzing said separated tumor cells to assess at least one of tumor cell number and type.

26. A method as claimed in claim 25, wherein a member of said specific binding pair is added to the separated cells to reverse aggregation of said sample, thereby facilitating analysis of said cells.

27. A method as claimed in claim 25, wherein said at least one biospecific reagent is selected from the group of consisting of monoclonal antibodies, polyclonal antibodies, detectably labeled antibodies, antibody fragments and single chain antibodies.

28. A method as claimed in claim 25 wherein said tumor cells are analyzed by a process selected from the group consisting of multiparameter flow cytometry, immunofluorescent microscopy, laser scanning cytometry, bright field base image analysis, capillary volumetry, manual cell analysis and automated cell analysis.

29. A method as claimed in claim 25, wherein said purified tumor cell-enriched fraction is examined to determine the degree of aggregation mediated by said first and second members of said specific binding pair.

30. A method as claimed in claim 24, wherein said specific binding pair is selected from the group consisting of biotin-streptavidin, antigen-antibody, receptor-hormone, receptor-ligand, agonist-antagonist, lectin-carbohydrate, Protein A-antibody Fc, and avidin-biotin, biotin analog-avidin, desthiobiotin-streptavidin, desthiobiotin-avidin, iminobiotin-streptavidin, and iminobiotin-avidin.

31. A method as claimed in claim 24, wherein said biospecific ligand is a monoclonal antibody.

32. A method as claimed in claim 31, wherein said biospecific ligand is an antibody having binding affinity for epithelial cell adhesion molecule.

33. A method as claimed in claim 24 wherein said biological sample is pretreated with an aggregation inhibiting agent to inactivate endogenous aggregation factors present in the sample prior to the preparation of said immunomagnetic suspension.

* * * * *

UNITED STATES PATENT AND TRADEMARK OFFICE
CERTIFICATE OF CORRECTION

PATENT NO.   : 6,623,982 B1                                         Page 1 of 1
DATED        : September 23, 2003
INVENTOR(S)  : Paul A. Liberti, Galla Chandra Rao and Leon W.M.M. Terstappen It is certified that error appears in the above-identified patent and that said Letters Patent is hereby corrected as shown below:

<u>Title page,</u>
Item [75], should read:
-- [75]   Inventors:      Paul A. Liberti, Huntingdon Valley, PA (US);
                          Galla Chandra Rao, Princeton, NJ (US);
                          Leon W. M. M. Terstappen, Huntingdon Valley, PA (US) --

Signed and Sealed this

Twenty-seventh Day of January, 2004

JON W. DUDAS
*Acting Director of the United States Patent and Trademark Office*